United States Patent [19]

Sarvazian et al.

[11] Patent Number: 5,542,298
[45] Date of Patent: Aug. 6, 1996

[54] METHOD FOR DETERMINING PHYSICAL STAGE PARAMETERS OF A MEDIUM AND AN APPARATUS FOR CARRYING OUT SAME

[76] Inventors: Armen P. Sarvazian, mikroraion "AB", 9,kv.36, Puschino na Oke, Serukhovsky raion, Moskovskaya oblast; Vladimir N. Belonenko, 10, kv. 6, poselok Razvilka, Leninsky raion, Moskovskaya oblast; Tigran V. Chalikian, prospekt Azatunian, 1, kv.28, Erevan, Armenia, all of Russian Federation

[21] Appl. No.: 435,531

[22] Filed: May 5, 1995

Related U.S. Application Data

[63] Continuation of Ser. No. 852,250, Jun. 2, 1992, abandoned.

[30] Foreign Application Priority Data

Aug. 24, 1990 [RU] Russian Federation ............... 4861972
May 30, 1991 [RU] Russian Federation ............... 4937760

[51] Int. Cl.⁶ .................................................. G01N 29/02
[52] U.S. Cl. ........................................... 73/597; 73/24.01
[58] Field of Search ............... 73/597, 590, 24.01–.05, 73/61.43–.49, 61.75, 61.79, 61.58, 584, 632, 645; 310/342; 422/82.01, 68.1, 256; 23/306

[56] References Cited

U.S. PATENT DOCUMENTS

| | | | |
|---|---|---|---|
| 3,916,672 | 11/1975 | Stansfeld | 73/24.05 |
| 4,166,394 | 9/1979 | Figura | 73/597 |
| 4,255,964 | 3/1981 | Morison | 73/24 |
| 4,763,513 | 8/1988 | Zacharias | 73/61 R |
| 4,907,453 | 3/1990 | Marlow | 73/584 |
| 5,060,507 | 10/1991 | Urmson et al. | 73/24.01 |
| 5,178,005 | 1/1993 | Peterson | 73/597 |

FOREIGN PATENT DOCUMENTS

| | | |
|---|---|---|
| 3420794 | 12/1984 | Germany . |
| 317931 | 11/1971 | U.S.S.R. . |
| 456996 | 3/1975 | U.S.S.R. . |
| 932389 | 5/1982 | U.S.S.R. . |
| 994975 | 2/1983 | U.S.S.R. . |
| 1026050 | 6/1985 | U.S.S.R. . |
| 1177697 | 9/1985 | U.S.S.R. . |
| 982442 | 12/1988 | U.S.S.R. . |
| 2149109 | 6/1985 | United Kingdom . |

*Primary Examiner*—Hezron E. Williams
*Assistant Examiner*—Helen C. Kwok
*Attorney, Agent, or Firm*—Ladas & Parry

[57] ABSTRACT

A method and apparatus for determining the physical state parameters of a medium under study generates oscillations in a reference medium and establishes the relation between one of the oscillatory process characteristics and a particular one of the parameters. The reference medium is then brought into contact with the medium under study, the oscillations generated again and the value of the particular parameter determined from changes in the oscillatory process characteristics. The oscillations generated are modulated ultrasonic or hypersonic oscillations. The oscillatory process characteristics include resonance frequency or Q-factor, propagation speed or absorption coefficient of the oscillations and relaxation frequency. Liquid, magnetorheological or electrorheological media are used as the reference medium.

117 Claims, 6 Drawing Sheets

METHOD FOR DETERMINING PHYSICAL STAGE PARAMETERS OF A MEDIUM AND AN APPARATUS FOR CARRYING OUT SAME

This is a continuation of application Ser. No. 07/852,250 filed on Jun. 2, 1992 now abandoned and International Application PCT/SU91/00171 filed on Aug. 23, 1991 and which designated the U.S.

TECHNICAL FIELD

The invention relates to the petroleum, petrochemical and chemical industries where the physico-chemical properties of fluids, substantially pressure, temperature, intensity of megnetic fields, and others are required to be measured or monitored by generating oscillations in the medium.

BACKGROUND ART

Known in the art is a method for measuring pressure by applying a reference voltage to the input of a piezoelectric sensor and determining the transformation ratio of the sensor depending on the pressure applied thereto during operation at a resonance frequency (SU A1 317,931).

Also known in the art is a method for monitoring the physical parameters of a liquid, comprising generating oscillations in the medium being monitored and receiving signals passing therethrough and determining the pressure from their characteristics (SU A1 456,996).

Known in the art is an apparatus for ultrasonically monitoring biological liquids, comprising a casing having a through conduit containing a measuring chamber and ultrasonic oscillation transducers provided coaxially at the opposite walls thereof (SU A1 932,389).

The drawbacks of the prior art methods and apparatuses are a low sensitivity and accuracy of measurement, which makes them unsuitable for use within a wide range of pressures and temperatures because of the non-rigid attachment of the ultrasonic oscillation transducers between the ends of the casing and the covers due to resilient spacers being inserted between the unstrained surface of the piezoelectric transducers and the mounting components.

The low accuracy of measurements is also due to the fact that the electrodes on piezoelectric plate surfaces unstrained by the medium under investigation do not coincide with the diameter of the measuring chamber, which results in the propagation of ultrasonic waves within the casing of the measuring chamber as well as in the medium under investigation.

DISCLOSURE OF THE INVENTION

It is an object of the present invention to develop an improved method for determining the physical parameters of a medium and an apparatus for performing the same, which has a design allowing it to expand the range of its functions and to improve the accuracy of measurements within a wide range of temperatures and pressures.

This object is achieved by a method for determining the state parameters of a medium, comprising generating oscillations, measuring the characteristics of the oscillatory process and detecting the desired parameter on their basis, further comprises generating oscillations in a reference medium element, detecting the relation between at least one of the oscillatory process characteristics and the parameter to be detected, bringing the reference element into contact with the medium under study, again generating oscillations in the element, and determining the value of the desired state parameter of the medium under study from changes in the oscillatory process characteristics in the reference medium element.

In addition, modulated oscillations are generated.

The oscillatory process characteristics used for the purposes of the invention include resonance frequency and/or Q-factor, and the propagation speed and/or absorption coefficient of oscillations; the relaxation frequency of the reference medium is further found, and the state parameters of the medium under study are determined from the relaxation frequency shift.

Ultrasonic, hypersonic and electromagnetic microwave oscillations are generated in the reference medium element.

A liquid medium corresponding to the medium under study in parameters is used as the reference medium element.

Also, an electrorheological and magnetorheological medium is used as the reference medium.

The reference medium is chosen and/or simulated with a linear relation between the oscillation propagation speed and the temperature, and/or with a linear relation between the elastic modulus and pressure.

The reference medium element is chosen or simulated depending on the medium under study, i.e., on its properties, state of aggregation, the conditions and objectives of the study, the parameter of the medium state to be measured (for example, pressure, temperature or specific volume) and the pattern of changes in physical properties. The reference medium is chosen to have the preferred (highest) sensitivity to the parameter being measured. This makes it possible to determine different state parameters within a wide measurement range and to study different media with a high accuracy.

Oscillatory processes used for determining state parameters according to the present method allow the physical properties of a medium (for example, elastic modulus and viscosity), as well as the state parameters (such as pressure) to be determined simultaneously using the same measuring equipment, making it possible to create optimal measurement conditions and to improve the efficiency of the method. Oscillation modulation helps improve the accuracy of measurement carried out at high frequencies with reference medium elements of a small size. The reference medium element in the form of a cavity and measurement of resonance oscillation frequency allow the accuracy to be enhanced, because the resonance oscillation frequency is determined with a high accuracy.

Studies in gases are carried out using the Q-factor, which helps expand the measurement range of, for example, pressure to a deep vacuum.

The speed and/or absorption coefficient of oscillations used as the oscillatory process characteristics measured make it possible, on the one hand, to improve the sensitivity of the method, because the absorption coefficient may change considerably even in response to small changes ($10^{-2}\%$ or less), for example, concentration of dissolved matter, and, on the other hand, to achieve optimal conditions and efficiency in measurements of the physical properties of media using oscillatory processes, because both the elastic properties (for example, compressibility) and pressure are determined from the propagation speed of oscillations, while the dissipative properties (for example, viscosity), and also, for example, pressure, are found from absorption magnitudes.

Measurements carried out at different oscillation frequencies yield good results because measurements of, for example, absorption in relation to the oscillation frequency help detect the relaxation frequency of the reference medium and monitor changes in the state parameters from shifts of the relaxation frequency under the effect of, for example, pressure. The reference medium element may be represented by, for example, a liquid having a relaxation dependent on the equilibrium established between dimers and monomers, or a liquid maintaining an intra-molecular relaxation process (isomeric relaxation); the relaxation frequency of such liquids does not depend on pressure, but changes with temperature variations, making it possible to simultaneously measure changes in pressure from an increase in the oscillation propagation speeds, and temperature from the values of $\alpha/f^2$ (or $\alpha/f$), wherein $\alpha$ is an absorption coefficient, and f is frequency.

Generation of ultrasonic oscillations helps improve the accuracy and sensitivity of the method which fact is due to the frequency values of the oscillations generated, the high ultrasound absorption values, the wavelengths, and to the ability of many media to relax within the ultrasonic frequency range. Furthermore, ultrasonic methods are suitable for determining simultaneously the physical properties of media, for example, the compressibility ratio, which fact permits the same equipment set to be used for determining the state parameters and physical properties of media.

Similarly, generation of hypersonic oscillations makes it possible to improve the sensitivity and accuracy of the method, minimize the size of the reference medium element, and to take measurements in thin films and layers, thereby expanding the possibilities of the method.

The liquid medium used as reference improves the accuracy and sensitivity of the method, because it makes for major changes in the propagation speed and absorption of oscillations depending on pressure and temperature. In turn, this expands the wide range of changes in frequency (for example, of a cavity) and the Q-factor, and-optimally during measurements in liquid media.

The employment of a magnetorheological and/or electrorheological medium helps improve the sensitivity of the method and to take precise measurements of medium state parameters and medium characteristics in the presence of a magnetic and electromagnetic fields.

The choice and/or simulation of a reference medium showing a linear relation between the propagation speed of oscillations and temperature improves the accuracy of the method in measuring the temperature of the medium under study, and helps create optimal conditions for measuring physical properties, because it allows only two reference points to be found on a line reflecting the relation between speed and temperature.

Similar objectives are attained when pressure is measured with the help of a reference medium element showing a linear relation between the elastic modulus and pressure.

To carry out the present method, each acoustic oscillation transducer in an apparatus for determining the physical state parameters of fluids, comprising a hollow casing having an orifice in the walls and provided with acoustic oscillation transducers on the ends thereof to define together with the casing a measuring chamber, and with fastening members, is rigidly secured at the perimeter between the casing end and a fastening member, the surface of each acoustic oscillation transducer in contact with the fluid under study being provided in the shape of a continuous electrode, and the electrode on the opposite surface of each acoustic oscillation transducer being coaxial with the measuring chamber and having an identical diameter therewith.

The above objective is further achieved by that the casing may contain more than more measuring chamber, the electrodes for which are provided on acoustic oscillation transducers common for all the chambers.

The measuring chambers are arranged symmetrically about the longitudinal axis of the casing, and also the measuring chambers are arranged in a line, one after another, their acoustic bases being optionally different.

The measuring chambers are insulated from the ambient by an elastic partition, and one of the measuring chambers is filled with a reference fluid.

Each of the fastening members has adjusting screws arranged symmetrically along the circumference thereof, and a sealing ring and a clamping ring are provided along the perimeter of each acoustic oscillation transducer.

The apparatus is placed in an autoclave to measure the characteristics of fluids under high pressures.

The expansion of functional possibilities and improved accuracy of measurement within a wide range of pressures and temperatures are achieved by securing each of the piezoelectric plates rigidly along the perimeter between the casing end and the fastening member.

The electrode being coaxial to the measuring chamber and having an identical diameter therewith, ultrasonic waves are only generated in the fluid filling the measuring chamber, thereby improving the accuracy of measurement.

With more than one measuring chamber arranged in the casing and with electrodes for all the chambers being provided on piezoelectric plates common for all the chambers, the characteristics of several samples (for example, solutions of different concentration) can be measured simultaneously. As a result, the functional possibilities of the apparatus are expanded and the accuracy of measurement is improved because all the samples are in identical conditions.

The location of the measuring chambers symmetrically about the longitudinal axis of the casing makes it possible to improve the accuracy of measurement because the symmetry helps minimize the temperature gradients between the chambers which are in identical temperature conditions. The positioning of the measuring chambers in line one after another allows the number of samples being measured to be increased and the range of pressures expanded, while the external diameter of the high-pressure vessel (autoclave) is reduced, thereby expanding the functional possibilities of the apparatus.

Insulation of the measuring chambers from the ambient by the elastic partition helps expand the functional possibilities of the apparatus because various liquids can be placed in the measuring chambers and separated from the pressure-transmitting liquid outside the apparatus or from the thermostatting liquid.

One of the measuring chambers being filled with a reference fluid, the accuracy of measurement is improved because the measurement results can be compared with the reference sample. Moreover, the measuring chamber filled with the reference fluid can also be used as a pressure (and/or temperature) sensor.

The adjusting screws arranged in each fastening member symmetrically along the circumference thereof allow the acoustic oscillation transducers to be tuned in parallel in the best possible manner and, therefore, the accuracy of measurement to be improved.

The sealing problem is solved by providing a sealing ring and a clamping ring along the perimeter of each acoustic oscillation transducer.

BRIEF DESCRIPTION OF DRAWINGS

The invention will be described below with reference to various specific embodiments thereof and the accompanying drawings, wherein.

DESCRIPTION OF THE PREFERRED EMBODIMENTS

The manner in which the method is carried out is best illustrated by the following description of the operation of an apparatus adapted for performing the method.

Figure 1:
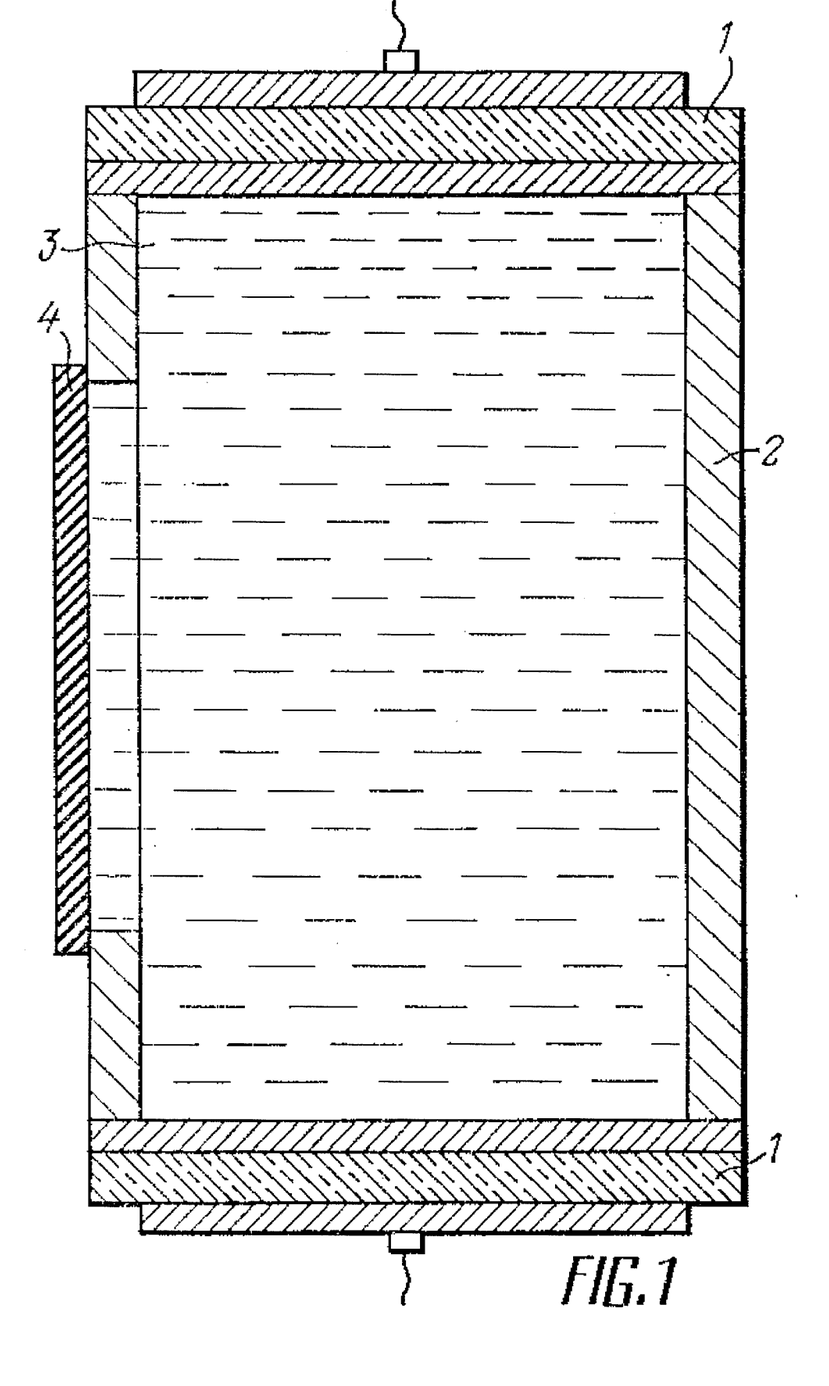
FIG. 1 is a schematic of an apparatus for carrying out a method, with a liquid reference medium.

FIG. 1 shows an apparatus comprising two piezoelectric crystal transducers 1 positioned in parallel with each other at the ends of a hollow casing 2 filled with a reference liquid 3 (reference medium element) and insulated from the ambient by an elastic partition 4.

Sine-wave acoustic oscillations of different frequencies, including ultra- or hypersonic oscillations, are generated in the reference medium; and their resonance frequency and/or Q-factor are determined at a definite temperature and atmospheric pressure. The apparatus is then placed in a vessel filled with, for example, gas, through which the pressure is transmitted to the reference medium element, and the relation between the resonance frequency, on the one hand, and/or Q-factor and pressure and/or, for example, evacuation degree, if the apparatus is to be used as a vacuum gauge, on the other, is determined. After the relation between the acoustic characteristics and the desired state parameters for the selected (simulated) reference liquid has been found, the apparatus is used as a pressure sensor (or, for example, a temperature sensor when the relation between the acoustic properties of the reference medium element and temperature is found). To take measurements in a medium under study, the apparatus is placed in a high-pressure vessel filled with a liquid, the pressure of which is to be measured. A change of pressure in the test liquid will cause a change in the reaction of the reference liquid which it transmits to the elastic partition which, in turn, results in a change in the resonance frequency and the Q-factor, the variations in which are used to determine pressure in the test medium.

Figure 2:
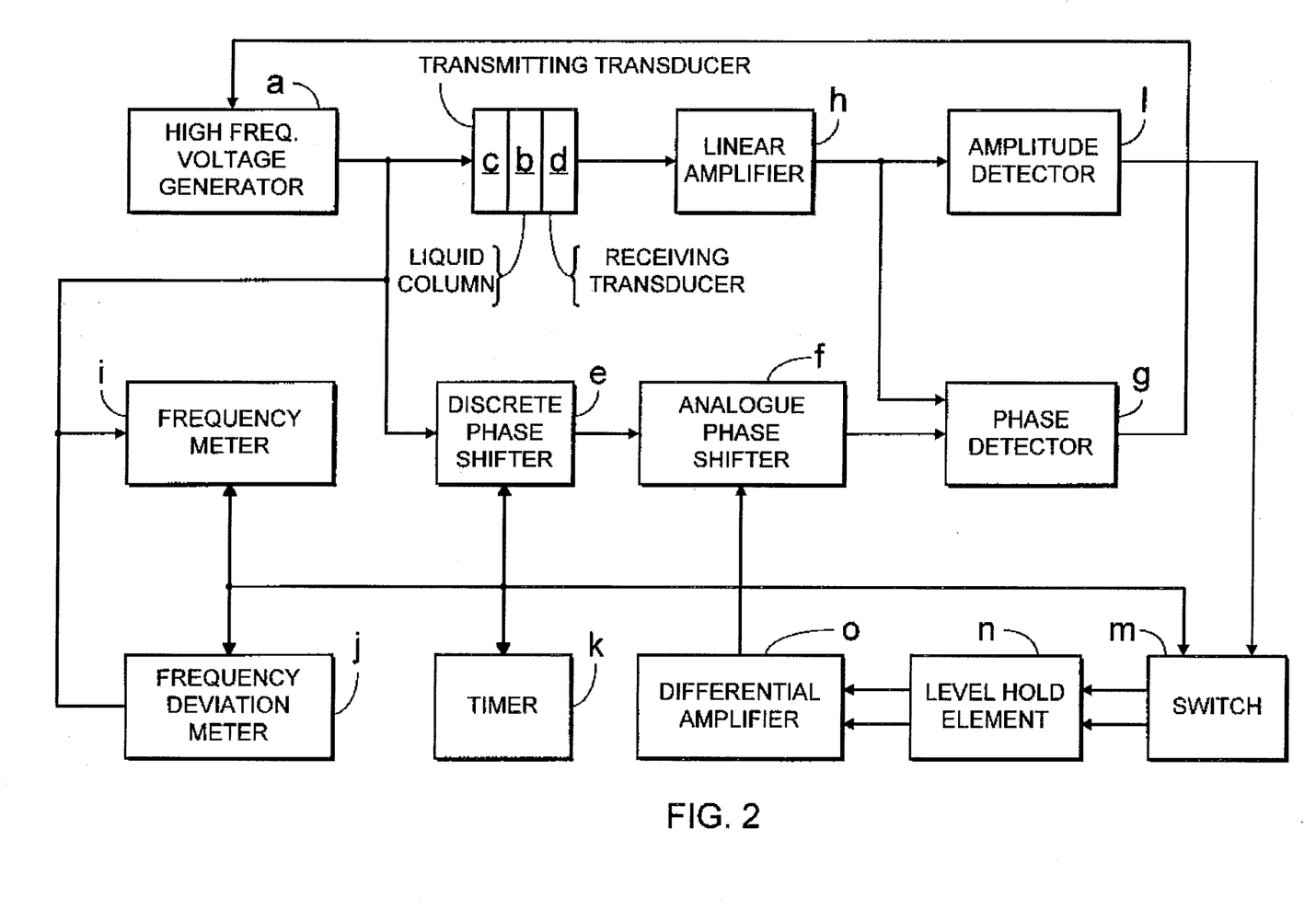
FIG. 2 is an electronic circuit diagram of an apparatus for taking precise measurements.

FIG. 2 is a circuit diagram of an apparatus used for precision measurements. The circuit includes:

a controlled sine-wave voltage generator (a); a liquid column (b) (3 in FIG. 1), twice-distilled water, in the present case, for temperature measurement; a transmitting transducer (c), a receiving transducer (d); a discrete phase shifter (e); an analogue phase shifter (f); a phase detector (g); a linear amplifier (h); a frequency meter (i); a frequency deviation meter (j); a timer (k); an amplitude detector (l); a switch (m); a level hold element (n); and a differential amplifier (o).

State parameters are determined as follows. High-frequency voltage at a frequency of 6.7 MHz is fed from the generator a (FIG. 2) to the transmitting transducer c, which serves to generate ultrasonic waves in the distilled water filling the apparatus. The ultrasonic waves are converted into electric oscillations by the receiving transducer d, amplified by the linear amplifier h and supplied to an input of the phase detector g. Another input of the phase detector g is supplied with a generator signal which has passed through the phase shifters e and f. A signal proportional to the phase difference of the input signals is fed from the output of the phase detector g to a control input of the generator a as a negative feedback signal. In this way, the apparatus operates automatically in a mode corresponding to the zero phase difference of the input signals of the phase detector g. On the basis of signals from the timer k, the discrete phase shifter e generates phase steps equal to ½ at a period of 1 sec. The amplitudes of the high-frequency voltage, corresponding to different states of the discrete phase shifter e, amplified by the linear amplifier h, are detected by the amplitude detector l and held at the respective inputs of the differential amplifier o by means of the switch m and level hold element n. The switch m and level hold element n are controlled by signals of the timer k. The voltage from the output of the differential amplifier o is supplied as a negative feedback signal to the control input of the analogue phase shifter f. The analogue phase shifter f is tuned so that the input voltage of the differential amplifier o equals zero. In this case, the arithmetic mean of frequencies corresponding to the two states of the discrete phase shifter, as measured by the frequency meter i, is equal to the central frequency $f_n$ of the resonance peak of the amplitude-frequency characteristic of the resonance device. The relation between $f_n$ and the desired medium state parameter (pressure) is found. The apparatus is placed in a high-pressure vessel containing, in the example under examination, a gas condensate, in which the pressure is to be measured and $f_n$ is measured, from which the desired pressure is found.

Following below is a description of an embodiment of the method for determining magnetic field intensity using the same apparatus. (FIGS. 1 and 2). The apparatus is filled with a magnetorheological liquid 3 (FIG. 1). A high-frequency voltage is supplied from the generator a (FIG. 2) to the transmitting transducer c, by means of which ultrasonic waves are excited in the magnetorheological liquid. Further on, the automatic tracking system operates similarly to the above, and the arithmetic mean of frequencies corresponding to the two states of the discrete phase shifter e is measured with the frequency meter i and found to be equal to the central frequency $f_n$ of the resonance peak of the amplitude-frequency characteristic. The difference between the frequencies corresponding to the two states of the discrete phase shifter f, measured by the frequency deviation meter j, is equal to the width of the resonance peak $\delta f_n$ proportional to the ultrasound absorption coefficient α in the cavity:

$$\frac{\alpha\lambda}{\pi} = \frac{\delta f_n}{f_n} = \frac{1}{Q}$$

wherein: $\lambda$ is the wavelength;
Q is the quality factor of the cavity; and
n is the serial number of the resonance peak.

The apparatus is placed in a magnetic field, and the reaction of the magnetorheological liquid to the intensity P of which shows in a change in the ultrasound absorption coefficient $\alpha$. After the functional connection has been established between the absorption $\alpha$ and the magnetic field intensity the apparatus is placed inside a turn that carries electric current (magnetic field intensity in the centre of the turn is H=J/2r, wherein J is current in the conductor and r is the turn radius) and the magnetic field intensity is measured.

Similarly, the apparatus described above is used to determine ultrasound velocity u in the medium filling the cavity, which is related to the frequency of the n-th resonance peak by the formula:

$$u = 2l\frac{f_n}{n}$$

wherein l is the length of the acoustic path.

The value of the state parameter being measured in the medium under study is found on the basis of the relation between the ultrasound velocity and the state parameter.

It is noteworthy that some other electronic circuits can be used to generate elastic oscillations in the medium with the help of the apparatus shown in FIG. 1.

Figure 12:
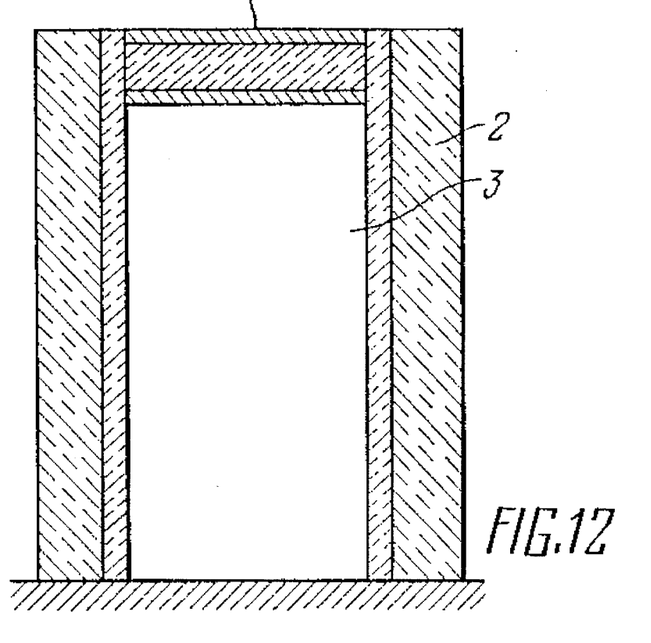
FIG. 12 is a schematic of an apparatus for determining the temperature of a metallic surface.

Below follows a description, by way of example, of a method for determining the temperature of a metal surface using the apparatus of FIG. 12. The apparatus comprises a piezoelectric transducer 1, a reference medium element 3 made of copper, and a heat-insulating shell 2 spray-coated with polyurethane. Alternating voltage is applied to the piezoelectric transducer 1 to generate ultrasonic oscillations in the reference medium element 3, and the relation between their characteristics (resonance frequency and Q-factor and/or propagation speed and absorption) and the temperature is found. Next, the reference medium element is brought into contact with the metal surface, and oscillations are again generated in the element, and the temperature is found from the values of the oscillatory process characteristics.

The apparatus of FIG. 1 is used to simultaneously measure (detect) pressure and temperature in the test medium. To this end, the cell in the casing between the piezoelectric crystals is filled with an inverse isomeric relaxation liquid, ultrasonic oscillations are generated in the reference medium element formed, and temperature values are found from the shift of the relaxation frequency (measured from the values of ultrasound absorption coefficient) and pressure is determined from the values of the volume elastic modulus (measured from ultrasound velocity values).

When it is required to measure, for example, the electromotive force (e.m.f.) of an electromagnetic field, the apparatus is filled with a magnetorheological (or electrorheological) liquid, acoustic oscillations are generated in the latter, and the resonance frequency and/or Q-factor is measured. The effect of the electromagnetic field alters the orientation and movement pattern of magnetic particles, causing changes in the resonance frequency and Q-factor, and the magnitude of these changes indicates the e.m.f. value of the electromagnetic field. The magnetic field intensity is determined in a similar manner.

Figure 3:
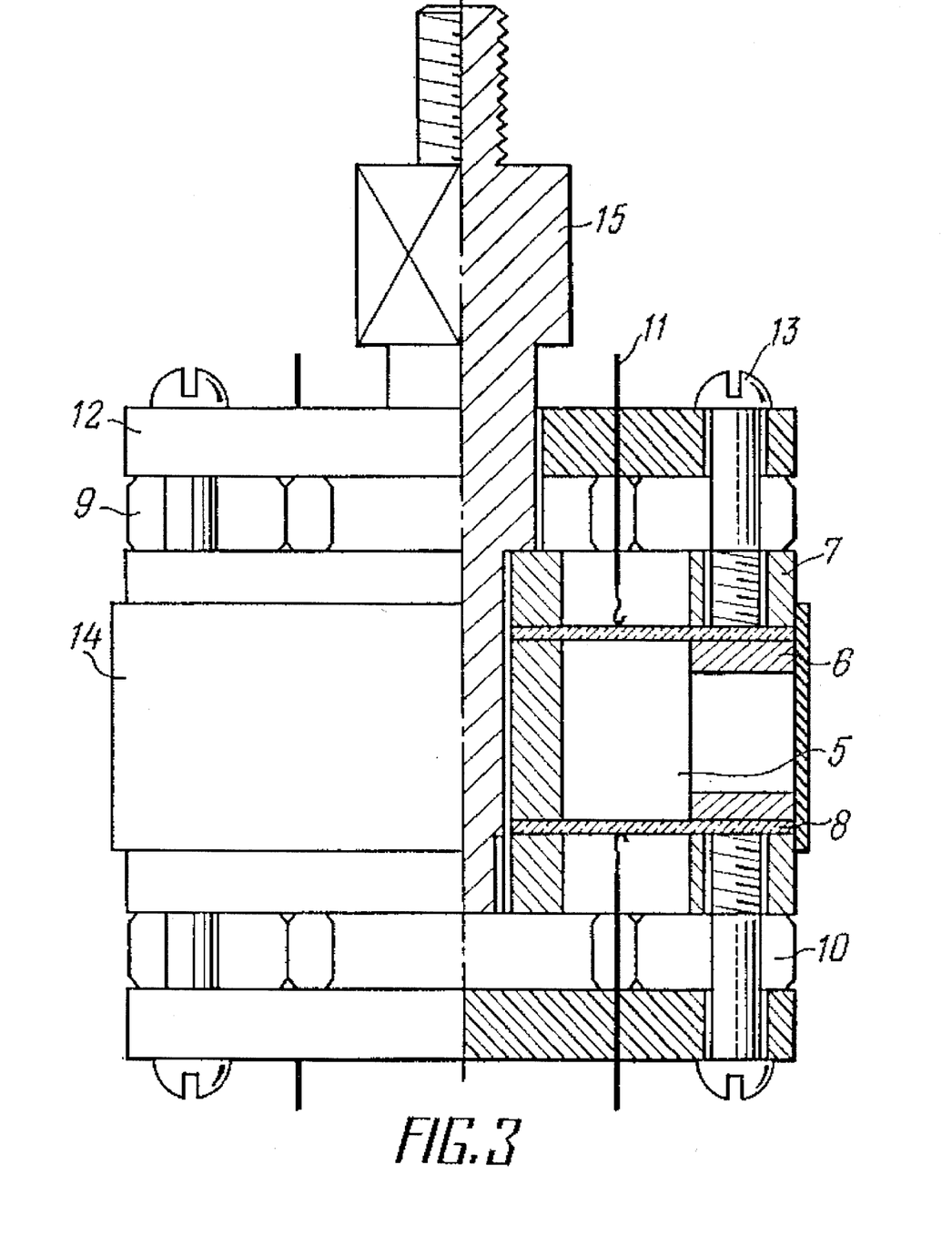
FIG. 3 is a schematic of an apparatus having four resonance ultrasonic chambers contained in a single casing.

An embodiment of the method using the apparatus of FIG. 3 is described below. The apparatus in this case has four measuring chambers 5 enclosed in a common all-metal casing 6. The chambers are identical and have identical characteristics. The piezoelectric transducers 8 of the cavities are pressed against the parallel ends of the casing 6 by clamping plates 7, bolts 10 and nuts 9. To reduce possible play in the chamber structure, the bolts 10 and a connecting member 15 extend through the casing 6 and clamping plates 7 with a tight fit. The contact electrodes 11 on the piezoelectric plates 8 are cut out so that ultrasonic waves are only generated in the liquids filling the measuring chambers 5. Since the electrodes are cut out on the piezoelectric plates common for all the cells, the resonance frequency of the transducers is identical in all the cells. Also identical is the reflection coefficient of the sound rebounding from the transducers. Electric signals are applied to the transducers through the contact electrodes 11 attached to the plates 12. Screws 13 are provided to ensure tight contact between the piezoelectric plates and the casing and to allow cavity adjustment. The measuring chambers are insulated from the ambient by a measuring partition 14.

The apparatus described is used to measure the properties of solutions at different concentrations. The following example describes a study of the concentration-related dependence of the adiabatic compressibility of amino acid solutions on pressure in isothermic conditions. Measurements are taken with amino acid preparations from Sigma, US. All the amino acids are in the L-stereo-isomeric form, without additional purification. The solutions are prepared in twice-distilled water. The solution concentrations are determined on the basis of dry weight. The preparations were pre-dried over $P_2O_5$. Measurements are taken at 25.0° C. in the following sequence: The measuring chambers 5 are filled with a reference medium, in the present case, with twice-distilled water.

This is not an obligatory step, however, because it is sufficient to fill only one chamber with the reference liquid. It makes it possible, however, to monitor the end results, because the procedure is actually equivalent to four parallel experiments and eliminates deformation change gradients in the measuring chambers.

Figure 4:
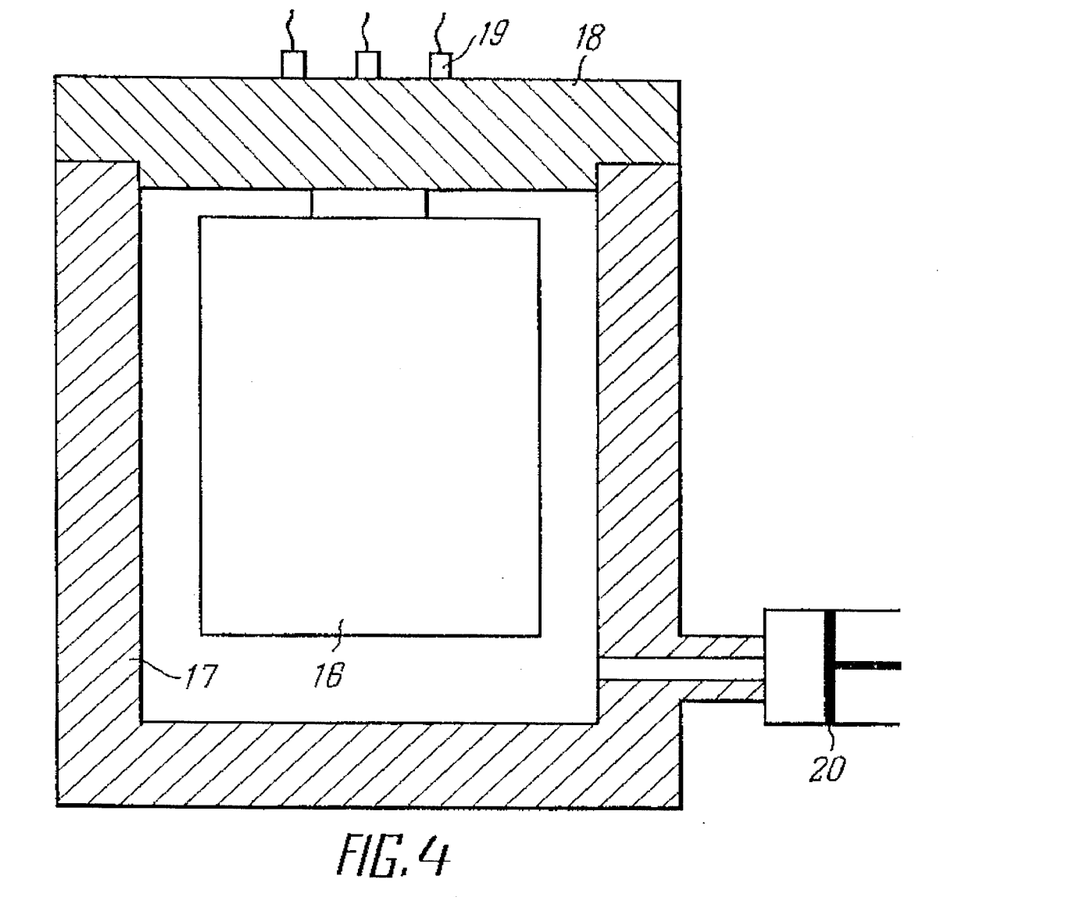
FIG. 4 is a schematic illustrating measurements carried out at high pressures.

After filling, the chambers are insulated by an elastic partition 14, and the apparatus (designated 16 in FIG. 4) is placed in a high-pressure vessel 17 (FIG. 4). The apparatus is fastened to the cover by a connecting member 15 (FIG. 3). The contact electrodes 11 are connected by high-pressure electrode inputs 19 (FIG. 4) in the cover 18 to instrumentation. The vessel 17 is filled with a pressure-transmitting liquid (ethyl alcohol in the current experiment), the pressure being built up by the displacement of a sealed plunger 20. Oscillations are generated in the chamber 5 (FIG. 3) and the oscillatory process characteristics—in the present case, resonance frequency, Q-factor, and ultrasound velocity and absorption coefficient—are measured depending on pressure at a constant temperature. The apparatus is then removed from the vessel, and the measuring chambers are emptied and filled with test samples, i.e., the reference medium (twice-distilled water) is retained in one of the cells, while the other three are filled with aqueous glycerol solutions at concentrations of 0.2, 0.4 and 0.6 mol/lit, respectively. Before being primed into the resonance chamber, the samples are held at a temperature equal to the cell temperature (25.0° C.). The chambers are insulated from the ambient by an elastic partition, and the apparatus is again placed in the high-pressure vessel 17 (FIG. 4). The assembled system is thermostatted at a temperature of 25.0° C.

The piston speed is preset by computer and readings are taken simultaneously from three solution-filled measuring chambers and from the chamber containing distilled water. The pressure is varied from 0.1 MPa to 100 MPa and measured with an accuracy of not less than 10 Pa. The apparatus is sensitive to pressure variations of ~0.05 Pa.

Then, pressure is measured in gases and in the deep vacuum region by the same apparatus. The measuring chamber containing the same reference liquid (twice-distilled water) is placed in the vessel 17 (FIG. 4) from which air is pumped out by a vacuum pump to a vacuum of $0.7 \cdot 10^{-2}$ Pa, which is determined by the present method by Q-factor measurements.

For comparison purposes, pressures were measured using a prior art method (SU A1 456,996).

The accuracy of pressure measurements was 0.8 MPa, and that of the sensitivity threshold, about 0.5 MPa, which is three to four orders below the results of the present method. Furthermore, the prior art method does not allow other properties of the samples to be studied simultaneously and studies to be carried out in vacuum. Even with four devices placed in a single high-pressure vessel to take measurements by the prior art method, favourable results cannot be obtained. For example, during studies of concentration-related dependence of increments of the nonlinear parameter of an aqueous glycerol solution, the accuracy was ~22%, whereas that of the present method was ~0.25%.

The present method provides a high accuracy and sensitivity and allows optimal conditions to be created for measurement of physical properties of media using oscillatory processes and the possibilities of the method to be expanded within a wide range of state parameter changes, including pressure ranging from deep vacuum ($10^{-3}$ Pa) to super-high levels of $~10^9$ or more.

The implementation of the method makes it possible to develop equipment for measuring state parameters of various media and minimize the size of measuring chambers (and devices). As a result, their metal weight is reduced considerably, their safety is improved in operation at high and super-high pressures, and a single set of instrumentation can be used for comprehensive studies.

Structurally, the apparatus (FIG. 5) comprises a hollow casing 21 having an opening 22 in the wall thereof, acoustic oscillation transducers 23 attached to the ends thereof and having electrodes 24, 25 and 39 which define with the casing 21 a measuring chamber 26, and fastening members 27. Each of the acoustic oscillation transducers 23 is rigidly secured at the perimeter between the end of the casing 21 and a fastening member 27.

Figure 5:
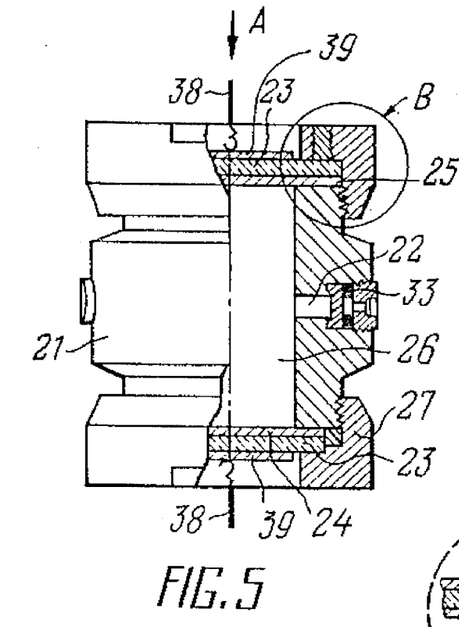
FIG. 5 illustrates the design of an apparatus for measuring acoustic characteristics of fluids.

The surface of each acoustic oscillation transducer 23 in contact with the test fluid is designed as a solid electrode 24, while the opposite surface of the transducer is an electrode 25 coaxial to the measuring chamber 26 and having an identical diameter therewith.

Figures 8, 9, 10:
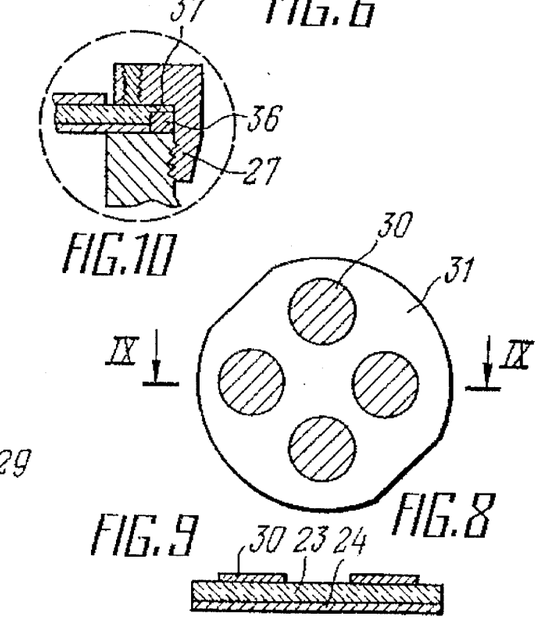
FIG. 8 is a top view of a transducer in FIG. 7.
FIG. 9 is a sectional view along IX—IX in FIG. 8.
FIG. 10 is a view of unit B in FIG. 5.

An alternative embodiment of the casing 28 contains four measuring chambers 29, electrodes 30 for which are provided on a common acoustic oscillation transducer 31 (FIGS. 8 and 9).

Figure 7:
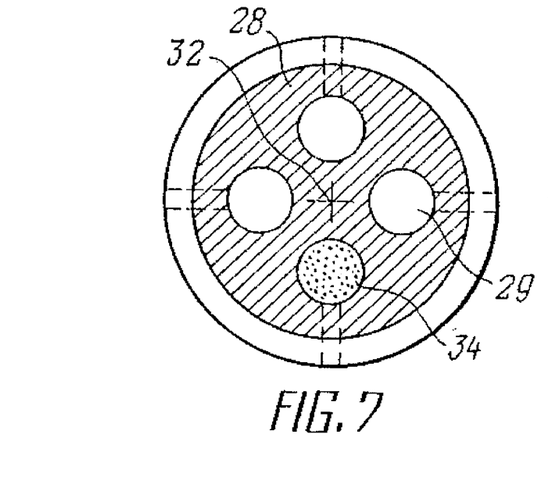
FIG. 7 is a sectional view along VII—VII in FIG. 5 for an embodiment having four measuring chambers in a casing.

Furthermore, the measuring chambers 29 are located symmetrically about the longitudinal axis 32 of the casing 28.

The measuring chambers are insulated from the ambient by an elastic partition 33 (FIG. 5).

Besides, one of the measuring chambers 34 is filled with a reference fluid.

Figure 6:
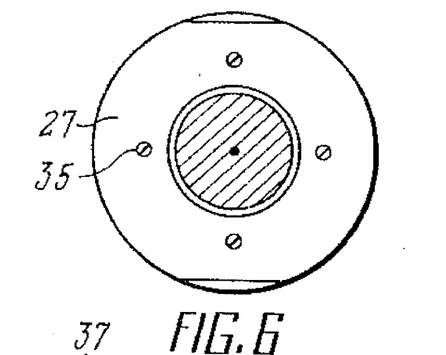
FIG. 6 is a top view of FIG. 5.

Each of the fastening members 27 carries adjusting screws 35 spaced symmetrically around the circumference (FIG. 6).

A sealing ring 36 and a clamping ring 37 are provided along the perimeter of each acoustic oscillation transducer 23 (FIG. 10).

Figure 11:
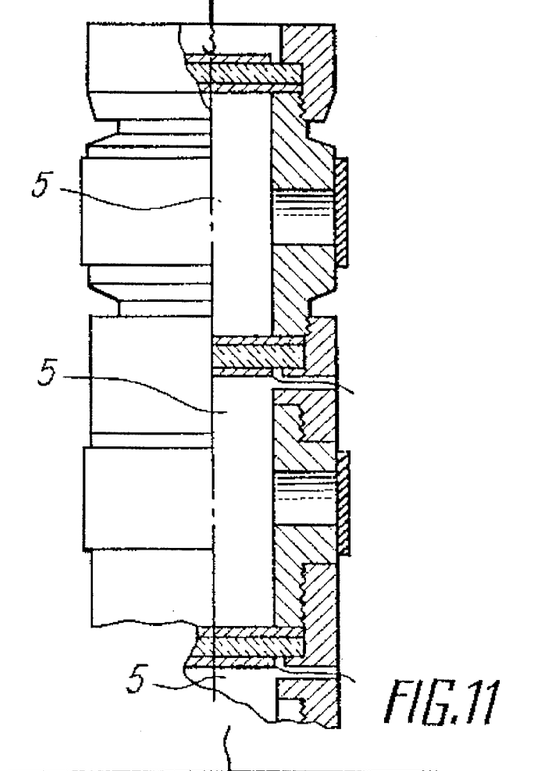
FIG. 11 shows a sequential arrangement of measuring chambers (one after another)

The measuring chambers 6 are arranged in line, one after another (FIG. 11).

The apparatus may be placed in an autoclave.

The apparatus is operated as follows: The electrodes 38 of the acoustic oscillation transducers are connected to a measuring unit (not shown), the measuring chamber 26 is filled with a test fluid and, in need, insulated from the ambient by an elastic partition 33, and the acoustic characteristics of the medium are measured.

Should amplitude-frequency characteristic signals show distortions, the acoustic oscillation transducers 23 are adjusted with the aid of adjusting screws 35.

When measurements are to be taken under high pressures, the apparatus is placed in an autoclave.

AN EMBODIMENT OF THE APPARATUS

Acoustic oscillation transducers are represented by plates of single lithium niobate crystals. Electrodes are provided on the opposite surfaces by gold sprayed thereon in vacuum. The casing and fastening members are made of titanium.

Electrodes are provided on the piezoelectric plates from gold as shown in FIG. 5, at the side opposite to the test liquid over the entire end surface, and on the opposite side, coextensive with the diameters of the openings in the casing. In a test when the concentration-related dependence of aqueous salt (NaCl) solutions is studied, one of the measuring chambers is filled with a reference liquid (distilled water), and the remaining three chambers are filled with test media, aqueous solutions of various concentrations. Before a sample is poured in, the chamber is carefully washed with distilled water and dried.

After the measuring chambers have been filled they are insulated from the ambient by a rubber seal ring as shown in FIG. 11.

In each fastening member, the adjusting screws (35) are provided symmetrically about the longitudinal axis of the casing (6).

The apparatus is placed in an autoclave and/or thermostat. An electric signal within a frequency range of 6 to 8 MHz is applied to the transducers via a system of electrodes, and measurements begin.

In high-pressure measurements, it is preferred to arrange the chambers in line one after another, as shown in FIG. 11. In this case, all the operations are identical to those described above. For reliable operation under pressures of 1,000 MPa the ratio of the external diameter to the internal diameter of the high-pressure vessel must be equal to about 4:1 (or 3:1).

The identity of the measuring chambers and their temperature and pressure conditions allow demands on thermostatting during differential measurements to be lowered sharply. To achieve a relative accuracy of $10^{-4}\%$ in velocity measurement in an aqueous solution at 25° C., the resonator chamber would be required to have a thermal stability of $6 \cdot 10^{-4}$° C. The task is greatly simplified by using a differential measurement method. Given the identical temperature and pressure conditions of the measuring chambers and their identity, it is only required to measure the frequency difference between the closest frequency harmonics of two cavities, one of which contains a test medium and the other, a reference solution having a close temperature velocity coefficient. This makes for a reduction of requirements on absolute thermal stability to 0.05° C., which is easily maintained by conventional laboratory thermostats.

The apparatus has broader functional possibilities and a higher accuracy within a wide range of pressures and temperatures. The present apparatus allows relative errors in measurements of sound velocity of $\pm 5 \cdot 10^{-6}$ and absorption coefficient of $4 \cdot 10^{-3}$ to be attained within a pressure range of 0.1 to 1,000 MPa.

A pilot specimen of the apparatus has been built and is currently used in practical measurements of acoustic characteristics of liquids (water and aqueous solutions of salts, proteins and amino acids, gas condensates, fuels, etc.).

INDUSTRIAL APPLICABILITY

The present invention is suitable for measuring acoustic characteristics of water and aqueous solutions of salts, proteins and amino acids, gas condensates, fuels and other liquids used in the oil and gas, petrochemical and chemical industries, in medicine, biology and many other fields.

We claim:

1. An apparatus for determining properties of a fluid medium at different concentrations of components comprising:

a first casing having first and second ends and a side wall, a first opening in said first casing in coaxial alignment therewith, a first piezoelectric plate arranged on said first end of said first casing perpendicular to a longitudinal axis thereof and rigidly secured to said first end along a perimeter thereof, a second piezoelectric plate arranged on said second end of said first casing perpendicular to said longitudinal axis thereof and rigidly secured to said second end along the perimeter thereof, a measuring chamber formed by said side wall of said first casing and said first and second piezoelectric plates, at least one opening in said side wall for admitting a fluid medium under study into said measuring chamber, a first electrode arranged on said first piezoelectric plate on a side of said measuring chamber and making contact with the whole surface of said first piezoelectric plate, a second electrode arranged on said first piezoelectric plate on a side opposite to said first electrode in coaxial alignment with said measuring chamber, the contour of said second electrode being coincidental with the contour of a cross section of said measuring chamber, a third electrode arranged on said second piezoelectric plate on a side of said measuring chamber and making contact with the whole surface of said second piezoelectric plate, a fourth electrode arranged on said second piezoelectric plate on a side opposite to said third electrode in coaxial alignment with said measuring chamber, the contour of said fourth electrode being coincidental with the contour of a cross section of said measuring chamber, a group of additional casings each having an axis coincidental with the axis of said first casing, and having a first end making contact with said second piezoelectric plate, and, each having a second end and a side wall, a second opening in each of said group of additional casings in coaxial alignment therewith, a plurality of additional piezoelectric plates, the number of said plurality of additional piezoelectric plates being equal to the number of said additional casings, each of said plurality of additional piezoelectric plates being in contact with said second end of a corresponding one of said additional casings and rigidly secured thereto along the perimeter thereof, a group of measuring chambers formed by respective side walls of the said additional casings and respective ones of said additional piezoelectric plates which are common to each two of said additional casings, an opening in each said side wall of each of said group of additional casings for admitting a fluid medium under study into each of said group of measuring chambers, a first plurality of electrodes, the number thereof being equal to the number of said additional casings, each of said first plurality of electrodes being arranged on a corresponding one of said additional piezoelectric plates on the side of a corresponding one of said group of measuring chambers thereof and making contact with the whole surface of said corresponding one of said additional piezoelectric plates thereof, a second plurality of electrodes respectively arranged on said additional piezoelectric plates on the sides thereof opposite to a corresponding one of said electrodes of the first plurality of electrodes, the contours thereof being coincidental with the contours of respective cross sections of said group of measuring chambers;

means connected with said first piezoelectric plate and said plurality of additional piezoelectric plates for generating oscillations in a reference medium contained in said measuring chamber and said group of measuring chambers; and means connected with said second piezoelectric plate for measuring oscillations in said reference medium contained in said measuring chamber and for determining properties of a fluid medium under study.

2. An apparatus for determining properties of a fluid medium at different concentrations of components comprising:

a casing having first and second ends and a side wall, an opening in said casing in alignment therewith, a first piezoelectric plate arranged on said first end of said casing perpendicular to a longitudinal axis thereof and rigidly secured to said first end along a perimeter thereof, a second piezoelectric plate arranged on said second end of said casing perpendicular to the longitudinal axis thereof and rigidly secured to said second end along the perimeter thereof, a measuring chamber formed by said side wall of the casing and said first and second piezoelectric plates, at least one opening in said side wall for admitting a fluid medium under study into said measuring chamber, a first electrode arranged on said first piezoelectric plate on a side of said measuring chamber and making contact with the whole surface of said first piezoelectric plate, a second electrode arranged on said first piezoelectric plate on a side opposite to said first electrode in coaxial alignment with said measuring chamber, the contour of said second electrode being coincidental with the contour of a cross section of said measuring chamber, a third electrode arranged on said second piezoelectric plate on a side of said measuring chamber and making contact with the whole surface of said second piezoelectric plate, a fourth electrode arranged on said second piezoelectric plate on a side opposite to said third electrode and in coaxial alignment with said measuring chamber, the contour of said fourth electrode being coincidental with the contour of a cross section of said measuring chamber;

means connected with said first piezoelectric plate for generating oscillations in a reference medium contained in said measuring chamber; and means connected with said second piezoelectric plate for measuring oscillations in said reference medium contained in said measuring chamber and for determining properties of a fluid medium under study.

3. An apparatus as claimed in claim 2, comprising:

at least one elastic sealing partition arranged on said side wall of said casing for sealing hermetically said measuring chamber thereof and maintaining physical contact with the fluid medium under study.

4. An apparatus as claimed in claim 2, in which a reference medium is used as said fluid medium under test.

5. An apparatus for determining properties of a fluid medium at different concentrations of components, comprising a casing having first and second ends and a side wall, at least two openings in said casing, each of said at least two openings having axes oriented parallel to an axis of said casing, a first piezoelectric plate secured to said first end of said casing perpendicular to a longitudinal axis thereof so that said first piezoelectric plate overlaps all of said at least two openings, a second piezoelectric plate secured to said second end of said casing perpendicular to the longitudinal axis thereof so that said second piezoelectric plate overlaps all of said at least two openings, a series of measuring chambers, the number of said measuring chambers being equal to the number of said openings, each of said measuring chambers being formed by said side wall of said casing, said side wall confining each of said openings and said first and second piezoelectric plates, a series of further openings, the number of said further openings being equal to said number of the measuring chambers, said further openings being in said side wall of said casing for admitting a fluid medium under test into said measuring chambers, a first electrode secured on said first piezoelectric plate on a side of said measuring chambers and making contact with the whole surface of said first piezoelectric plate, a first series of further electrodes, the number of said first series of further electrodes being equal to the number of said measuring chambers, each of said first series of further electrodes being secured on said first piezoelectric plate on a side opposite to said first electrode and in coaxial alignment with said measuring chambers, the contour of each of said first series of further electrodes being coincidental with the contour of a cross section of a corresponding one of said measuring chambers, a second electrode secured on said second piezoelectric plate on a side of said measuring chambers and making contact with the whole surface of said second piezoelectric plate, a second series of still further electrodes, the number of said still further electrodes being equal to the number of said measuring chambers, each of said still further electrodes being secured on said second piezoelectric plate on a side opposite to said second electrode and in coaxial alignment with said measuring chambers, the contour of each of said still further electrodes being coincidental with the contour of a cross section of a corresponding one of said measuring chambers;

means connected with said first piezoelectric plate and said plurality of additional piezoelectric plates for generating oscillations in a reference medium contained in said measuring chamber and said group of measuring chambers; and means connected with said second piezoelectric plate for measuring oscillations in said reference medium contained in said measuring chamber and for determining properties of a fluid medium under study.

6. An apparatus as claimed in claim 5, in which said measuring chambers are arranged symmetrically relative to the longitudinal axis of said casing.

7. An apparatus as claimed in claim 5, having an elastic sealing partition located on said side wall of said casing for hermetically sealing said measuring chambers and maintaining physical contact of said fluid medium under test contained in each of said measuring chambers with a surrounding medium.

8. An apparatus as claimed in claim 5, having a series of elastic sealing partitions, the number of said elastic sealing partitions being equal to the number of said further openings, said elastic sealing partitions being respectively secured in said further openings for hermetically sealing said measuring chambers and maintaining physical contact of said fluid medium under test contained in each of said measuring chambers with a surrounding medium.

9. An apparatus as claimed in claim 5, having two sealing rings and two locking rings mounted along the perimeter of each of said first and second electrodes.

10. An apparatus as claimed in claim 9, having at least two fastening members for securing said piezoelectric plates to said first and second ends of said casing and at least two adjusting screws for each of said fastening members, said screws being arranged symmetrically relative to the longitudinal axis of said casing.

11. A method for determining properties of a fluid medium under study at different component concentrations comprising the steps of:

filling a reference measuring chamber with a reference medium, said reference measuring chamber having a first piezoelectric plate at one end and a second piezoelectric plate at an opposite end in a manner such that an axis of said reference measuring chamber is perpendicular to planes in which said plates are arranged, generating oscillations in said reference medium by using said first piezoelectric plate, disposing said reference measuring chamber in a fluid medium under study, and determining characteristics of an oscillatory process in said reference measuring chamber by measuring oscillations occurring in said reference medium resulting from oscillations generated by said first piezoelectric plate by using said second piezoelectric plate, said characteristics being used to determine properties of said fluid medium under study in relation with component concentration of said fluid medium under study.

12. A method as claimed in claim 11, in which one component of said fluid medium under study is said reference medium.

13. A method as claimed in claim 11, in which a magnetorheologic liquid is used as said reference medium.

14. A method as claimed in claim 11, in which a liquid capable of intramolecular relaxation is used as said reference medium.

15. A method as claimed in claim 11, in which a liquid capable of rotary isometric relaxation is used as said reference medium.

16. A method as claimed in claim 11, in which a mixture of at least two components of said fluid medium under study is used as said reference medium.

17. A method as claimed in claim 13, in which said reference medium is a mixture capable of relaxation due to an equilibrium between dimers and monomers.

18. A method as claimed in claim 11, in which at least one component of said fluid medium under study, of which a bulk elastic modulus is linearly pressure dependent, is used as said reference medium.

19. A method as claimed in claim 11, in which at least one component of said fluid medium under study, of which a propagation speed of oscillations is linearly temperature dependent, is used as said reference medium.

20. A method as claimed in claim 11, in which said oscillations are modulated.

21. A method as claimed in claim 11, in which said oscillations are in the ultrasonic frequency range.

22. A method as claimed in claim 11, in which said oscillations in said reference measuring chamber are in the hypersonic frequency range.

23. A method as claimed in claim 11, wherein a relaxation frequency is used as a determinable characteristic of said oscillatory process.

24. A method as claimed in claim 11, in which the resonance frequency is used as a determinable characteristic of the oscillatory process.

25. A method as claimed in claim 11, in which the Q-factor is used as a determinable characteristic of the oscillatory process.

26. A method as claimed in claim 11, in which the wave propagation speed is used as a determinable characteristic of the oscillatory process.

27. A method as claimed in claim 11, in which the wave absorption coefficient is used as a determinable characteristic of the oscillatory process.

28. A method as claimed in claim 11, which comprises building up pressure in said reference measuring chamber by applying an external force to an elastic sealing partition located on a side surface of said reference measuring chamber, said force being in the range between 0.1 MPa and 1000 MPa.

29. A method as claimed in claim 11, which further comprises measuring pressure in said reference measuring chamber.

30. A method as claimed in claim 11, which further comprises measuring a temperature in said reference measuring chamber.

31. A method for determining properties of a fluid medium at different component concentrations comprising the steps of:

filling a reference measuring chamber with a reference medium, said reference measuring chamber having a first piezoelectric plate at one end and a second piezoelectric plate at an opposite end in a manner such that an axis of said reference measuring chamber is perpendicular to planes in which said plates are arranged, positioning at least one additional reference measuring chamber between said first and second piezoelectric plates so that an axis of said at least one additional reference measuring chamber is parallel to said axis of said reference measuring chamber, filling said at least one additional reference measuring chamber with said reference medium, generating oscillations in said reference measuring chambers by using said first piezoelectric plate, disposing said reference measuring chambers in a fluid medium under study, and determining characteristics of an oscillatory process in each of said reference measuring chambers by measuring oscillations occurring in said reference medium resulting from oscillations generated by said first piezoelectric plate by using said second piezoelectric plate, said characteristics being used to determine properties of said fluid medium under study in relation with component concentration of said fluid medium under study.

32. A method as claimed in claim 31, which comprises using distilled water as said reference medium, determining the amplitude-frequency characteristic of the oscillatory process in said reference measuring chambers at different values of frequency and phase, determining the phase-frequency characteristic of the oscillatory process in said reference measuring chambers at different values of phase and frequency, choosing a constant for each measurement of said frequency of the phase characteristic, measuring at said phase frequency characteristic at least one of the characteristics of the oscillatory process, which is chosen from a group consisting of resonance frequency, relaxation frequency, Q-factor, wave propagation speed and wave absorption coefficient, as a function of time, said at least one of the characteristics of the oscillatory process being used to determine the temperature of said fluid medium under study.

33. A method as claimed in claim 32, which comprises determining the pressure in said fluid medium under study.

34. The method according to claim 31, wherein one component of said fluid medium under study is said reference medium.

35. The method according to claim 31, wherein a magnetorheologic liquid is used as said reference medium.

36. The method according to claim 31, wherein a liquid capable of intramolecular relaxation is used as said reference medium.

37. The method according to claim 31, wherein a liquid capable of rotary isomeric relaxation is used as said reference medium.

38. The method according to claim 31, wherein a mixture of at least two components of said fluid medium under study is used as said reference medium.

39. The method according to claim 31, wherein said reference medium is a mixture capable of relaxation due to an equilibrium between dimers and monomers.

40. The method according to claim 31, wherein at least one component of said fluid medium under study, of which a bulk elastic modulus is linearly pressure dependent, is used as said reference medium.

41. The method according to claim 31, wherein at least one component of said fluid medium under study, of which a propagation speed of oscillations is linearly temperature dependent, is used as said reference medium.

42. The method according to claim 31, wherein said oscillations are modulated.

43. The method according to claim 31, wherein said oscillations are in the ultrasonic frequency range.

44. The method according to claim 31, wherein said oscillations in said reference measuring chamber are in the hypersonic frequency range.

45. The method according to claim 31, wherein a relaxation frequency is used as a determinable characteristic of said oscillatory process.

46. The method according to claim 31, wherein a resonance frequency is used as a determinable characteristic of said oscillatory process.

47. The method according to claim 31, wherein a Q-factor is used as a determinable characteristic of the oscillatory process.

48. The method according to claim 31, wherein a wave propogation speed is used as a determinable characteristic of the oscillatory process.

49. The method according to claim 31, wherein a wave absorption coefficient is used as a determinable characteristic of the oscillatory process.

50. The method as claimed in claim 31, further including the step of building up pressure in said reference measuring chamber and said at least one additional reference measuring chamber by applying an external force to an elastic sealing partition located on a side surface of said reference measuring chamber and said at least one additional reference measuring chamber, said force being in the range between 0.1 MPa and 1000 MPa.

51. The method according to claim 31, further including the step of measuring pressure in said reference measuring chamber.

52. The method according to claim 31, further including the step of measuring a temperature in said reference measuring chamber.

53. A method for determining properties of a fluid medium under study at different component concentrations comprising the steps of:

filling a reference measuring chamber with a reference medium, said reference measuring chamber having a first piezoelectric plate at one end and a second piezoelectric plate at an opposite end in a manner such that an axis of said reference measuring chamber is perpendicular to planes in which said plates are arranged, said reference medium subjected to substantially identical temperature and having an approximately identical velocity coefficient as a temperature and velocity coefficient of said fluid medium under study, in addition to said reference measuring chamber, placing one or more measuring chambers between said first and second piezoelectric plates so that an axis of each of said one or more measuring chambers is parallel to said axis of said reference measuring chamber, filling each of said one or more measuring chambers with varying concentrations of said fluid medium under study, generating oscillations in said reference measuring chamber and said one or more measuring chambers by using said first piezoelectric plate, determining characteristics of an oscillatory process in said reference measuring chamber and said one or more measuring chambers by measuring oscillations occurring in said reference medium resulting from oscillations generated by said first piezoelectric plate by using said second piezoelectric plate, said characteristics being used to determine properties of said fluid medium under study in relation with component concentration of said fluid medium under study.

54. A method as claimed in claim 53, which comprises building up pressure in said reference measuring chamber and one of said one or more measuring chambers by applying an external force to an elastic sealing partition located on a side surface of said reference measuring chamber and said one of said one or more measuring chambers, said force being in the range between 0.1 MPa and 1000 MPa.

55. A method as claimed in claim 53, which further comprises:

disposing said reference measuring chamber and said said one or more measuring chambers in said fluid medium under study and filling said one or more measuring chambers with said fluid medium under study during said disposing.

56. The method according to claim 53, wherein one component of said fluid medium under study is said reference medium.

57. The method according to claim 53, wherein a magnetorheologic liquid is used as said reference medium.

58. The method according to claim 53, wherein a liquid capable of intramolecular relaxation is used as said reference medium.

59. The method according to claim 53, wherein a liquid capable of rotary isomeric relaxation is used as said reference medium.

60. The method according to claim 53, wherein a mixture of at least two components of said fluid medium under study is used as said reference medium.

61. The method according to claim 60, wherein said reference medium is a mixture capable of relaxation due to an equilibrium between dimers and monomers.

62. The method according to claim 53, wherein at least one component of said fluid medium under study, of which a bulk elastic modulus is linearly pressure dependent, is used as said reference medium.

63. The method according to claim 53, wherein at least one component of said fluid medium under study, of which a propagation speed of oscillations is linearly temperature dependent, is used as said reference medium.

64. The method according to claim 53, wherein said oscillations are modulated.

65. The method according to claim 53, wherein said oscillations are in the ultrasonic frequency range.

66. The method according to claim 53, wherein said oscillations in said reference measuring chamber are in the hypersonic frequency range.

67. The method according to claim 53, wherein a relaxation frequency is used as a determinable characteristic of said oscillatory process.

68. The method according to claim 53, wherein a resonance frequency is used as a determinable characteristic of said oscillatory process.

69. The method according to claim 53, wherein a Q-factor is used as a determinable characteristic of the oscillatory process.

70. The method according to claim 53, wherein a wave propogation speed is used as a determinable characteristic of the oscillatory process.

71. The method according to claim 53, wherein a wave absorption coefficient is used as a determinable characteristic of the oscillatory process.

72. The method according to claim 53, further including the step of measuring pressure in said reference measuring chamber.

73. The method according to claim 53, further including the step of measuring a temperature in said reference measuring chamber.

74. A method for determining properties of a fluid medium at different component concentrations comprising the following operations:

filling a reference measuring chamber with a reference medium, said reference measuring chamber having a first piezoelectric plate at one end and a second piezoelectric plate at an opposite end in a manner such that an axis of said reference measuring chamber is perpendicular to planes in which said plates are arranged, in addition to said reference measuring chamber, placing at least one measuring chamber in alignment with said reference measuring chamber wherein said at least one measuring chamber is placed between said second piezoelectric plate and a corresponding additional piezoelectric plate so that axes of said at least one measuring chambers are perpendicular to the planes of said additional piezoelectric plates and filling said at least one measuring chamber with a fluid medium under study, generating oscillations in said reference measuring chamber by using said first piezoelectric plate and generating oscillations in said at least one measuring chamber by using said additional piezoelectric plate located alternately from said first piezoelectric plate in respect of said second piezoelectric plate, determining characteristics of an oscillatory process in said reference measuring chamber and in one of said at least one measuring chambers adjacent to said reference measuring chamber by measuring oscillations occurring in said reference medium resulting from oscillations generated by said first piezoelectric plate by using said second piezoelectric plate and determining characteristics of an oscillatory process occurring in another of said at least one measuring chamber by using a corresponding additional piezoelectric plate associated with a said corresponding additional piezoelectric plate used for generating said oscillations for determining properties of said fluid medium under study in relation with a component concentration of said fluid medium under study.

75. A method as claimed in claim 74, in which said at least one measuring chamber has a corresponding measurement base.

76. The method according to claim 74, wherein one component of said fluid medium under study is said reference medium.

77. The method according to claim 74, wherein a magnetorheologic liquid is used as said reference medium.

78. The method according to claim 74, wherein a liquid capable of intramolecular relaxation is used as said reference medium.

79. The method according to claim 74, wherein a liquid capable of rotary isomeric relaxation is used as said reference medium.

80. The method according to claim 74, wherein a mixture of at least two components of said fluid medium under study is used as said reference medium.

81. The method according to claim 80, wherein said reference medium is a mixture capable of relaxation due to an equilibrium between dimers and monomers.

82. The method according to claim 74, wherein at least one component of said fluid medium under study, of which a bulk elastic modulus is linearly pressure dependent, is used as said reference medium.

83. The method according to claim 74, wherein at least one component of said fluid medium under study, of which a propagation speed of oscillations is linearly temperature dependent, is used as said reference medium.

84. The method according to claim 74, wherein said oscillations are modulated.

85. The method according to claim 74, wherein said oscillations are in the ultrasonic frequency range.

86. The method according to claim 74, wherein said oscillations in said reference measuring chamber are in the hypersonic frequency range.

87. The method according to claim 74, wherein a relaxation frequency is used as a determinable characteristic of said oscillatory process.

88. The method according to claim 74, wherein a resonance frequency is used as a determinable characteristic of said oscillatory process.

89. The method according to claim 74, wherein a Q-factor is used as a determinable characteristic of the oscillatory process.

90. The method according to claim 74, wherein a wave propogation speed is used as a determinable characteristic of the oscillatory process.

91. The method according to claim 74, wherein a wave absorption coefficient is used as a determinable characteristic of the oscillatory process.

92. The method according to claim 74, further including the step of building up pressure in said reference measuring chamber and said at least one measuring chamber by applying an external force to an elastic sealing partition located on a side surface of said reference measuring chamber and said at least one measuring chamber, said force being in the range between 0.1 MPa and 1000 MPa.

93. The method according to claim 74, further including the step of disposing said reference measuring chamber and said at least one measuring chamber in said fluid medium under study and filling said at least one said measuring chamber with said fluid medium under study during said disposing.

94. The method according to claim 74, further including the step of measuring pressure in said reference measuring chamber.

95. The method according to claim 74, further including the step of measuring a temperature in said reference measuring chamber.

96. A method for determining properties of a fluid medium at different component concentrations comprising the following operations:

filling a reference measuring chamber with a reference medium, said reference measuring chamber having a first piezoelectric plate at one end and a second piezoelectric plate at an opposite end in a manner such that an axis of the reference measuring chamber is perpendicular to planes in which said plates are arranged, in addition to said reference measuring chamber, placing at least one measuring chamber in alignment with said reference measuring chamber wherein said at least one measuring chamber is placed between said second piezoelectric plate and a corresponding additional piezoelectric plate so that axes of said at least one measuring chamber are perpendicular to said planes of said additional piezoelectric plates and are aligned with each other, and filling said at least one measuring chamber with said reference medium, disposing said reference measuring chamber and said at least one measuring chamber in a fluid medium under study, generating oscillations in said reference measuring chamber by using said first piezoelectric plate and generating oscillations in said at least one measuring chamber by using said additional piezoelectric plate located alternately from said first piezoelectric plate in respect of said second piezoelectric plate, determining characteristics of an oscillatory process in said reference measuring chamber and in one of said at least one measuring chamber adjacent to said reference measuring chamber by measuring oscillations occurring in said reference medium resulting from oscillations generated by said first piezoelectric plate by using said second piezoelectric plate and, determining characteristics of an oscillatory process occurring in the other of said at least one measuring chamber by using corresponding additional piezoelectric plates each plate being associated with a said corresponding additional piezoelectric plate used for generating said oscillations for determining properties of said fluid medium under study in relation with a component concentration of said fluid medium under study.

97. The method according to claim 96, wherein one component of said fluid medium under study is said reference medium.

98. The method according to claim 96, wherein a magnetorheologic liquid is used as said reference medium.

99. The method according to claim 96, wherein a liquid capable of intramolecular relaxation is used as said reference medium.

100. The method according to claim 96, wherein a liquid capable of rotary isomeric relaxation is used as said reference medium.

101. The method according to claim 96, wherein a mixture of at least two components of said fluid medium under study is used as said reference medium.

102. The method according to claim 101, wherein said reference medium is a mixture capable of relaxation due to an equilibrium between dimers and monomers.

103. The method according to claim 96, wherein at least one component of said fluid medium under study, of which a bulk elastic modulus is linearly pressure dependent, is used as said reference medium.

104. The method according to claim 96, wherein at least one component of said fluid medium under study, of which a propagation speed of oscillations is linearly temperature dependent, is used as said reference medium.

105. The method according to claim 96, wherein said oscillations are modulated.

106. The method according to claim 96, wherein said oscillations are in the ultrasonic frequency range.

107. The method according to claim 96, wherein said oscillations in said reference measuring chamber are in the hypersonic frequency range.

108. The method according to claim 96, wherein a relaxation frequency is used as a determinable characteristic of said oscillatory process.

109. The method according to claim 96, wherein a resonance frequency is used as a determinable characteristic of said oscillatory process.

110. The method according to claim 96, wherein a Q-factor is used as a determinable characteristic of the oscillatory process.

111. The method according to claim 96, wherein a wave propogation speed is used as a determinable characteristic of the oscillatory process.

112. The method according to claim 96, wherein a wave absorption coefficient is used as a determinable characteristic of the oscillatory process.

113. The method as claimed in claim 96, further including the step of building up pressure in said reference measuring chamber and said at least one measuring chamber by applying an external force to an elastic sealing partition located on a side surface of said reference measuring chamber and said at least one measuring chamber, said force being in the range between 0.1 MPa and 1000 MPa.

114. The method according to claim 96, further including the step of measuring pressure in said reference measuring chamber.

115. The method according to claim 96, further including the step of measuring a temperature in said reference measuring chamber.

116. The method as claimed in claim 96, further including the steps of:

using distilled water as said reference medium, determining the amplitude-frequency characteristic of the oscillatory process in said reference measuring chambers at different values of frequency and phase, determining the phase-frequency characteristic of the oscillatory process in said reference measuring chambers at different values of phase and frequency, choosing a constant for each measurement of said frequency of the phase characteristic, measuring at said phase frequency characteristic at least one of the characteristics of the oscillatory process, which is chosen from a group consisting of resonance frequency, relaxation frequency, Q-factor, wave propagation speed and wave absorption coefficient, as a function of time, said at least one of the characteristics of the oscillatory process being used to determine the temperature of said fluid medium under study.

117. The method according to claim 116, which comprises determining the pressure in said fluid medium under study.

* * * * *

UNITED STATES PATENT AND TRADEMARK OFFICE
CERTIFICATE OF CORRECTION

PATENT NO.  :   5,542,298
DATED       :   August 6, 1996
INVENTOR(S) :   Armen P. SARVAZIAN, et al.

It is certified that error appears in the above-indentified patent and that said Letters Patent is hereby corrected as shown below:

On title page, insert --[73] Assignee:
VSEROSSIISKY NAUCHNO-ISSLEDOVATELSKY INSTITUT PRIRODNYKH
GAZOV I GAZOVYKH TEKHNOLOGY ROSSIISKOGO AKTSIONERNOGO
OBSCHESTVA "GAZPROM"
LENINSKYU RAION,
                  MOSKÓVSKAYA OBLAST,
POSELOK RAZVILKA, RUSSIAN FEDERATION Signed and Sealed this Sixth Day of January, 1998

*Attest:*

BRUCE LEHMAN

*Attesting Officer*     *Commissioner of Patents and Trademarks*